(12) United States Patent
Lafontaine

(10) Patent No.: US 6,656,199 B1
(45) Date of Patent: Dec. 2, 2003

(54) MAGNETIC CLAMP ASSEMBLY FOR AN ELONGATED FLEXIBLE MEDICAL DEVICE

(75) Inventor: Daniel M. Lafontaine, Plymouth, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 293 days.

(21) Appl. No.: 09/645,222

(22) Filed: Aug. 24, 2000

(51) Int. Cl.[7] ................................................. A61B 5/00
(52) U.S. Cl. ........................................ 606/191; 606/192
(58) Field of Search ............................ 606/1, 191, 192, 606/198; 600/12, 13, 101, 102, 114, 116–118, 585; 604/96.01, 164.04, 164.13, 165.01, 165.02, 167.06, 174, 264, 523, 533–535, 585, 921; 128/912; 5/600, 601, 906

(56) References Cited

U.S. PATENT DOCUMENTS

| | | | |
|---|---|---|---|
| 5,005,590 A | * 4/1991 | Eldridge et al. | 206/364 |
| 5,195,538 A | * 3/1993 | Eldridge et al. | 206/364 |
| 5,269,759 A | * 12/1993 | Hernandez et al. | 604/96.01 |
| 5,464,023 A | 11/1995 | Viera | |
| 5,487,729 A | * 1/1996 | Avellanet et al. | 604/96.01 |
| 5,542,938 A | * 8/1996 | Avellanet et al. | 604/96.01 |
| 5,555,893 A | 9/1996 | Hackett et al. | 128/772 |
| 5,606,980 A | * 3/1997 | Calhoun et al. | 604/96.01 |
| 5,623,943 A | 4/1997 | Hackett et al. | 128/772 |
| 5,624,430 A | * 4/1997 | Eton et al. | 606/1 |
| 5,706,827 A | * 1/1998 | Ehr et al. | 604/96.01 |
| 5,776,080 A | 7/1998 | Thome et al. | |
| 5,830,183 A | 11/1998 | Krieger | 604/96 |
| 5,931,818 A | 8/1999 | Werp et al. | |
| 5,954,707 A | 9/1999 | Kanesaka et al. | 604/523 |
| 6,013,038 A | * 1/2000 | Pflueger | 600/585 |
| 6,068,121 A | * 5/2000 | McGlinch | 206/364 |
| 6,471,172 B1 | * 10/2002 | Lemke et al. | 600/12 |

FOREIGN PATENT DOCUMENTS

WO  WO 95/21566  8/1995
WO  WO 99/42167  8/1999

* cited by examiner

*Primary Examiner*—Gloria M. Hale
(74) *Attorney, Agent, or Firm*—Westman, Champlin & Kelly, P.A.

(57) ABSTRACT

A magnetic clamp assembly for an elongated flexible medical device. The clamp assembly includes magnetic clamp members operably coupled to clamp a portion of the flexible medical device to secure the medical device during treatment.

34 Claims, 11 Drawing Sheets

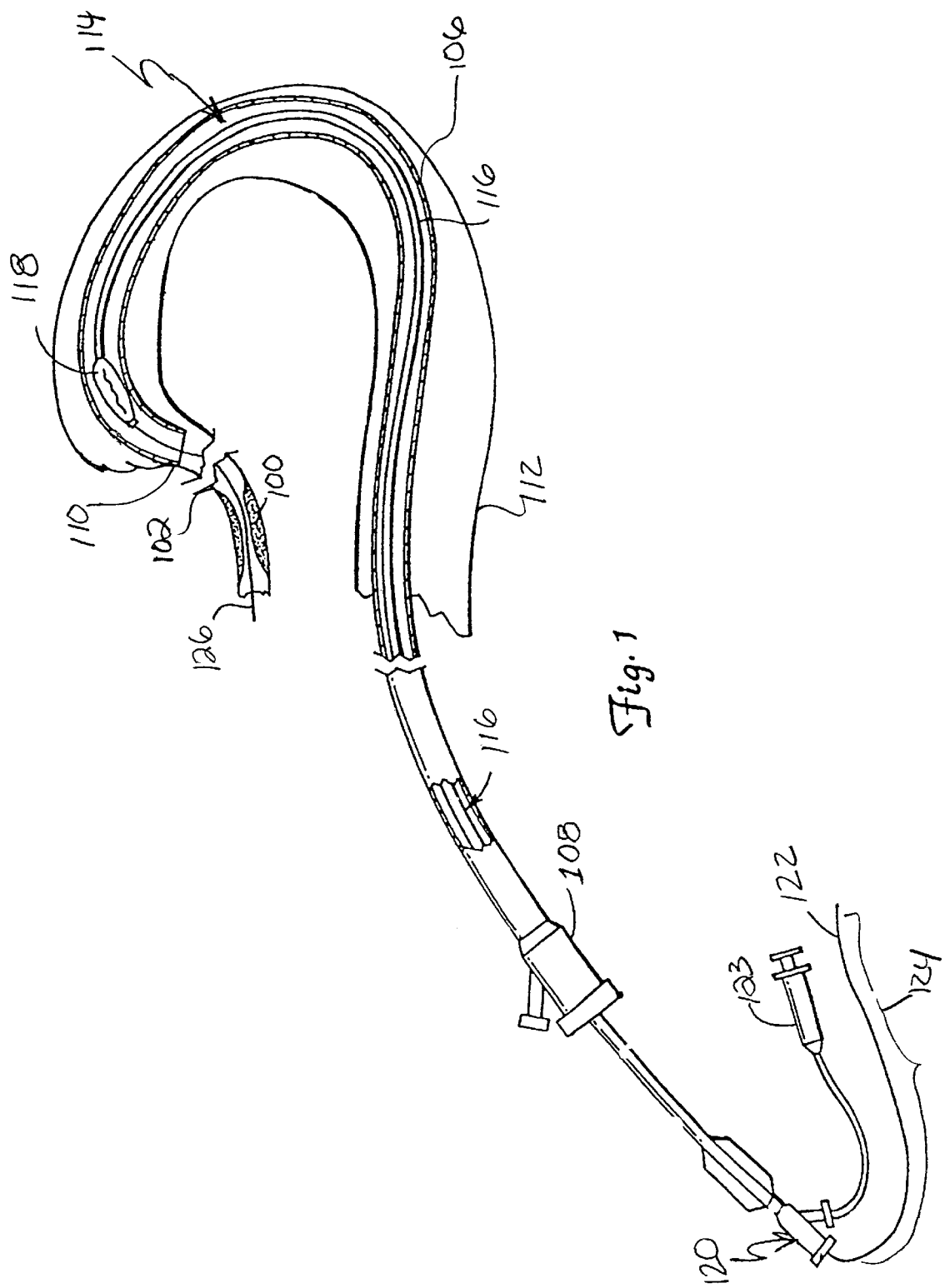

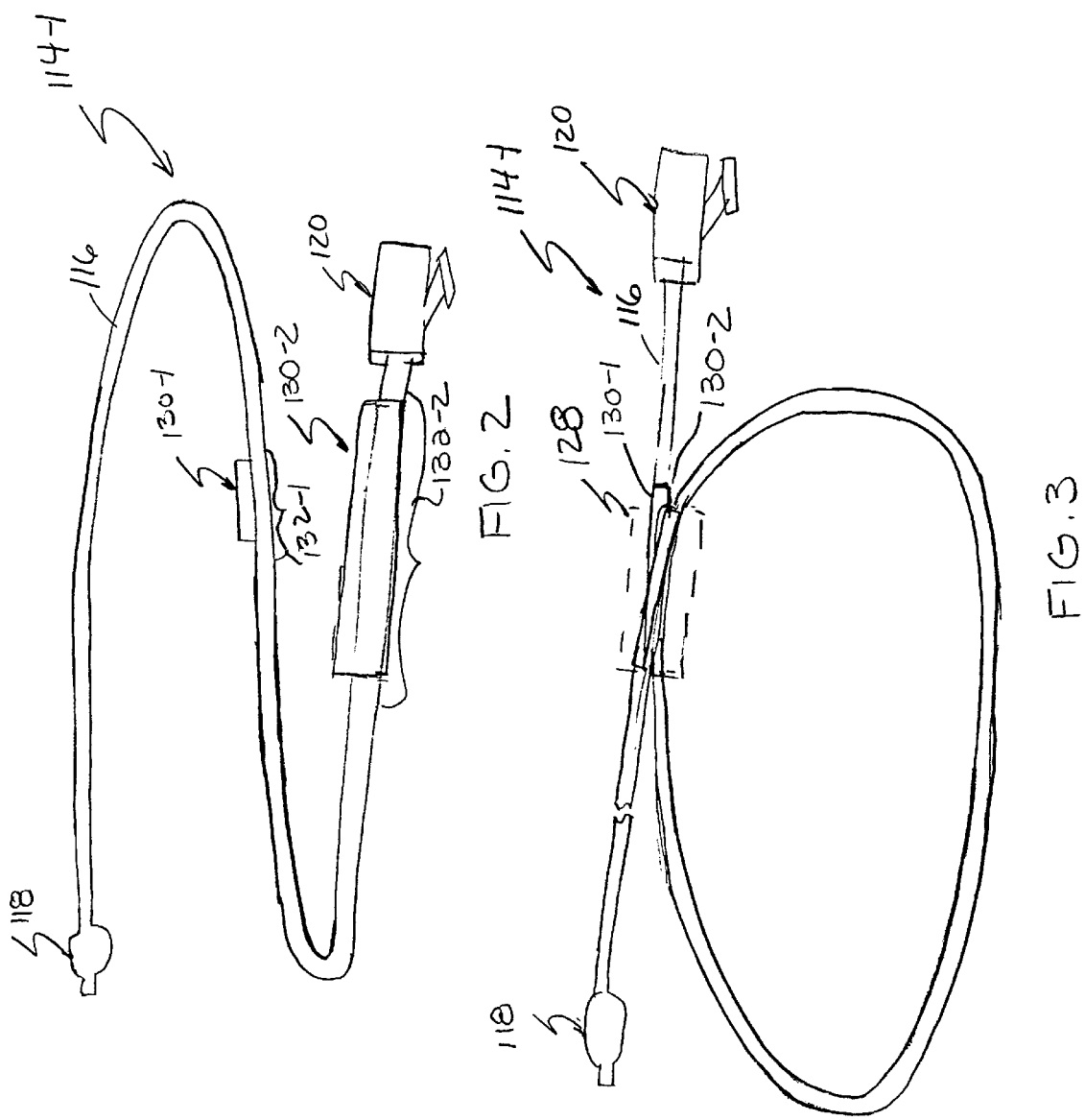

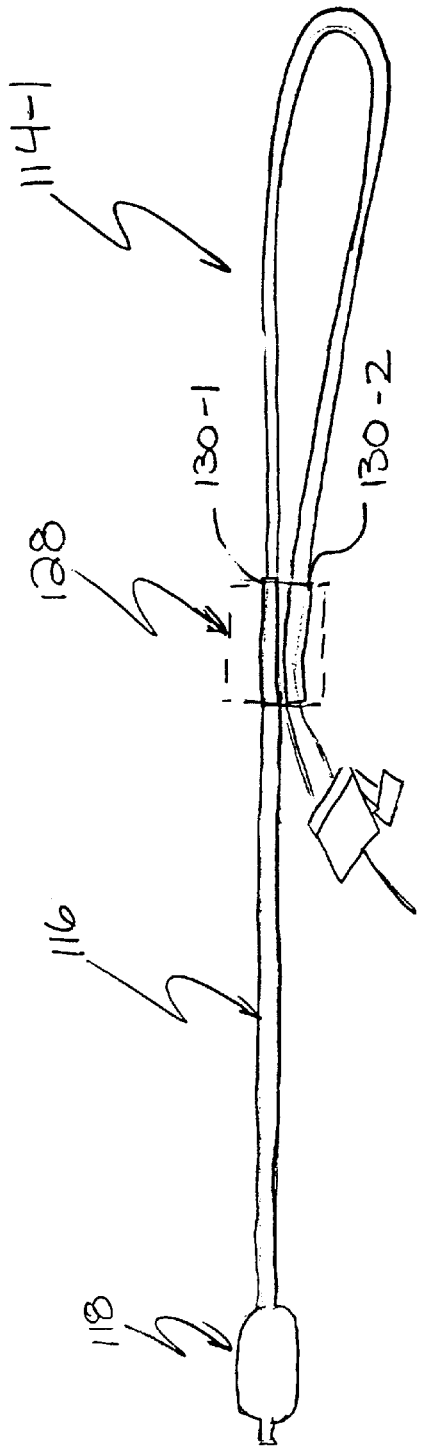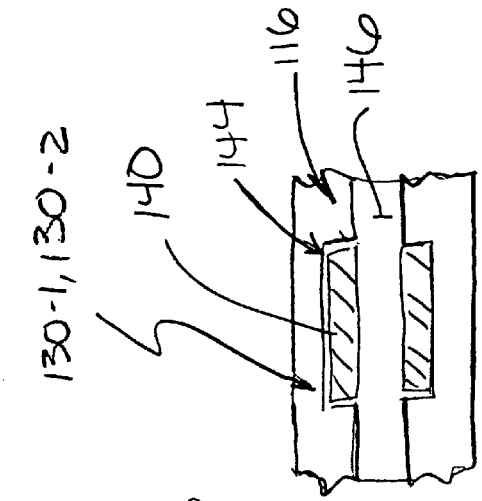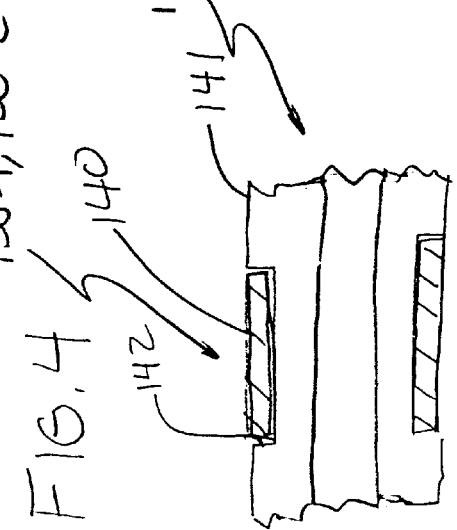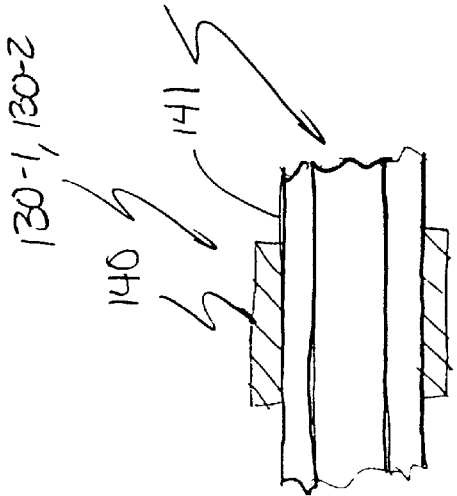

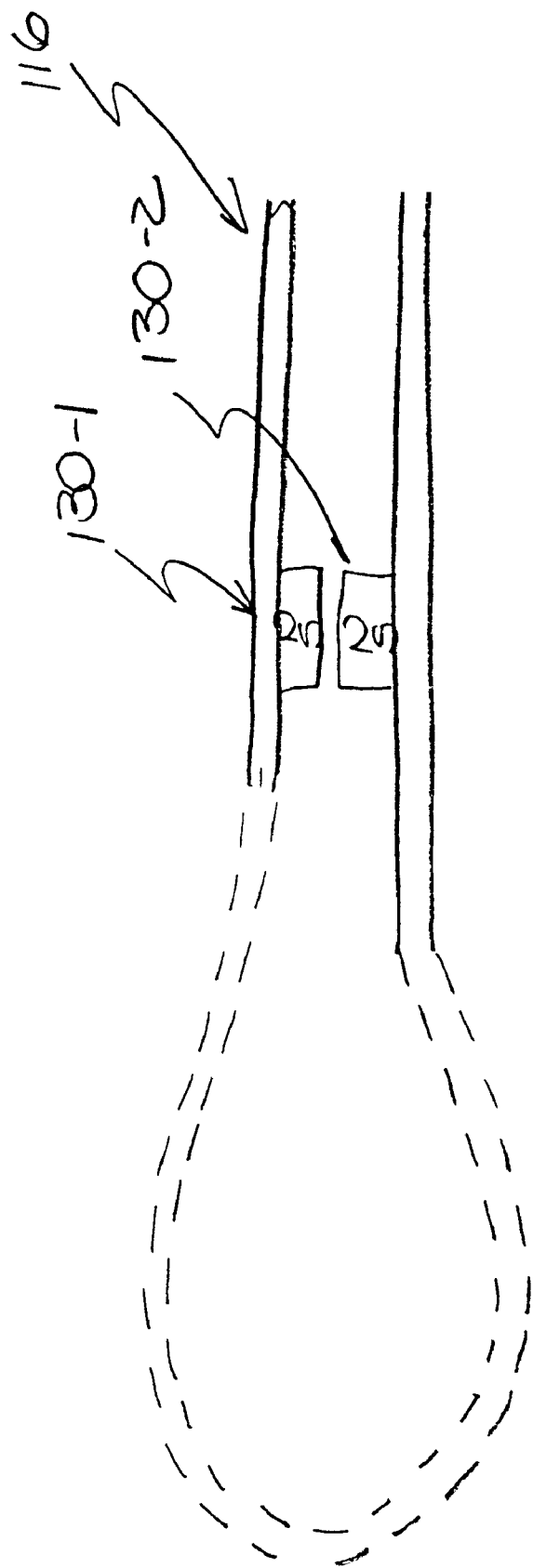

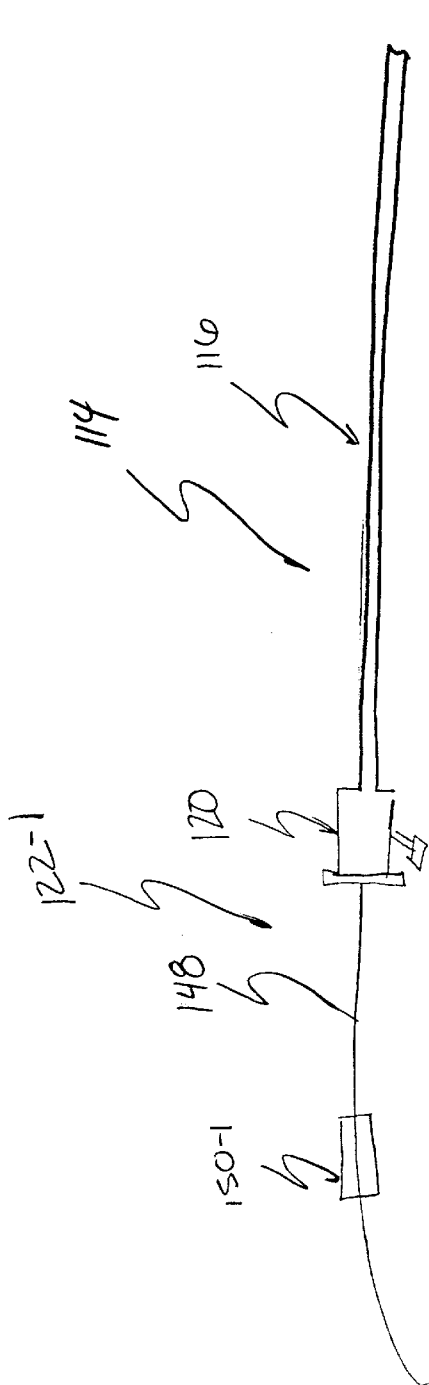
FIG. 8
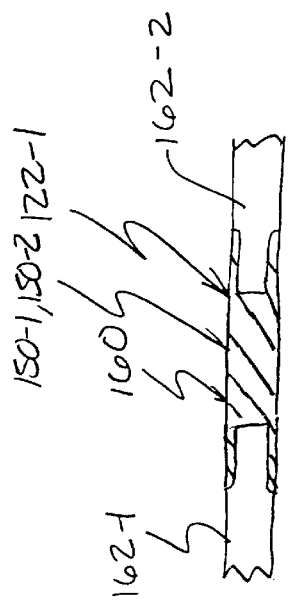
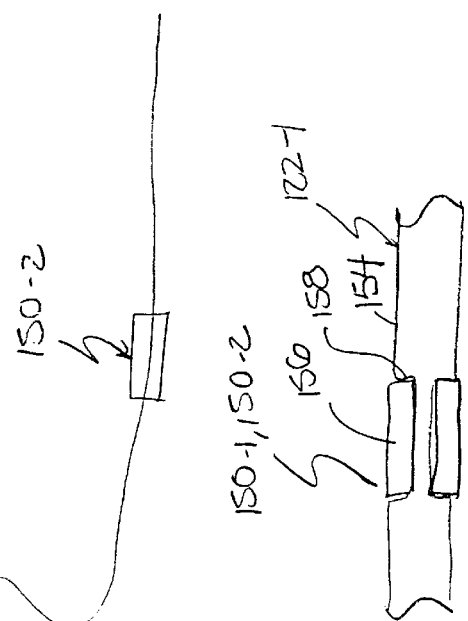
FIG. 10-2
FIG. 10-3

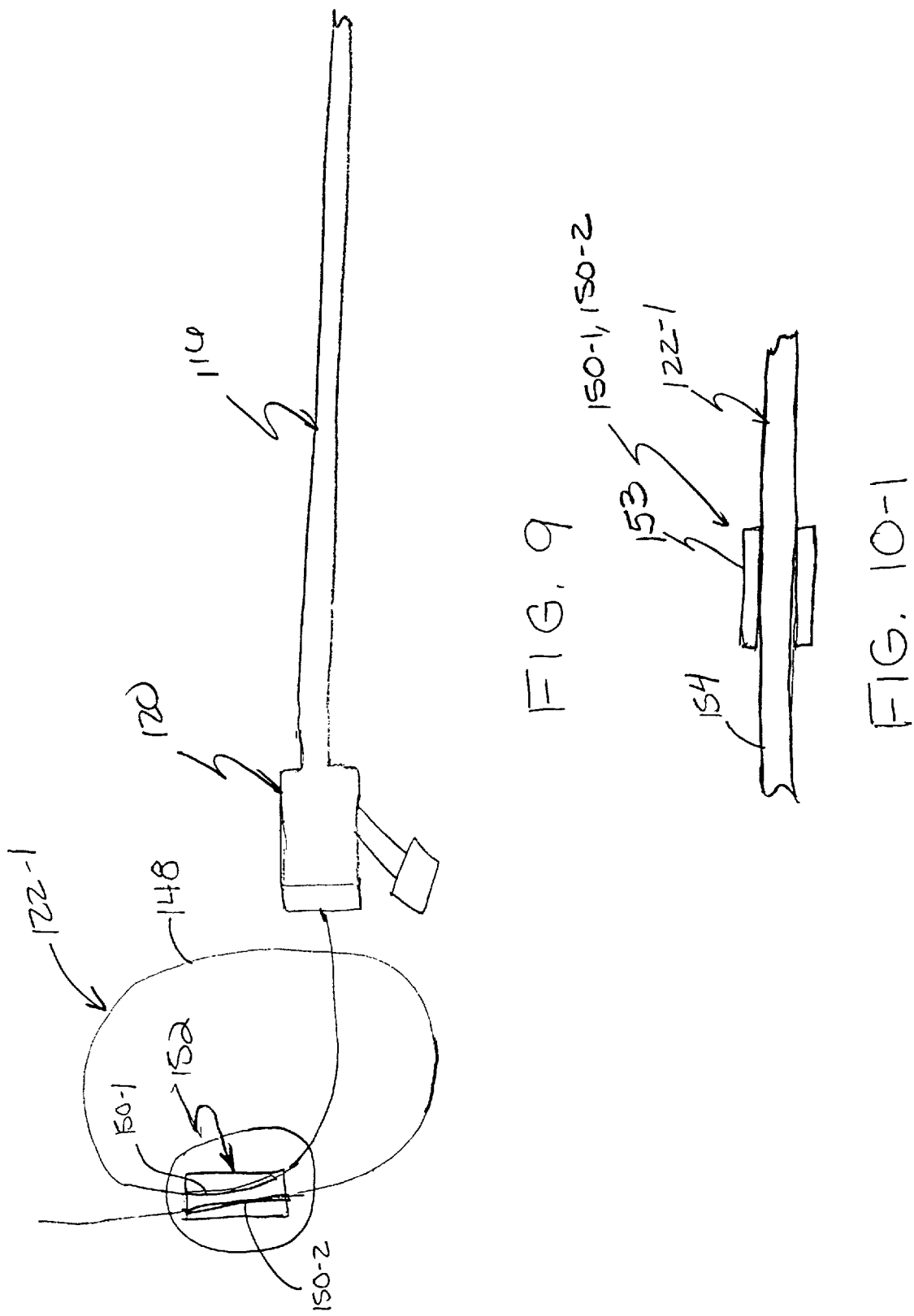

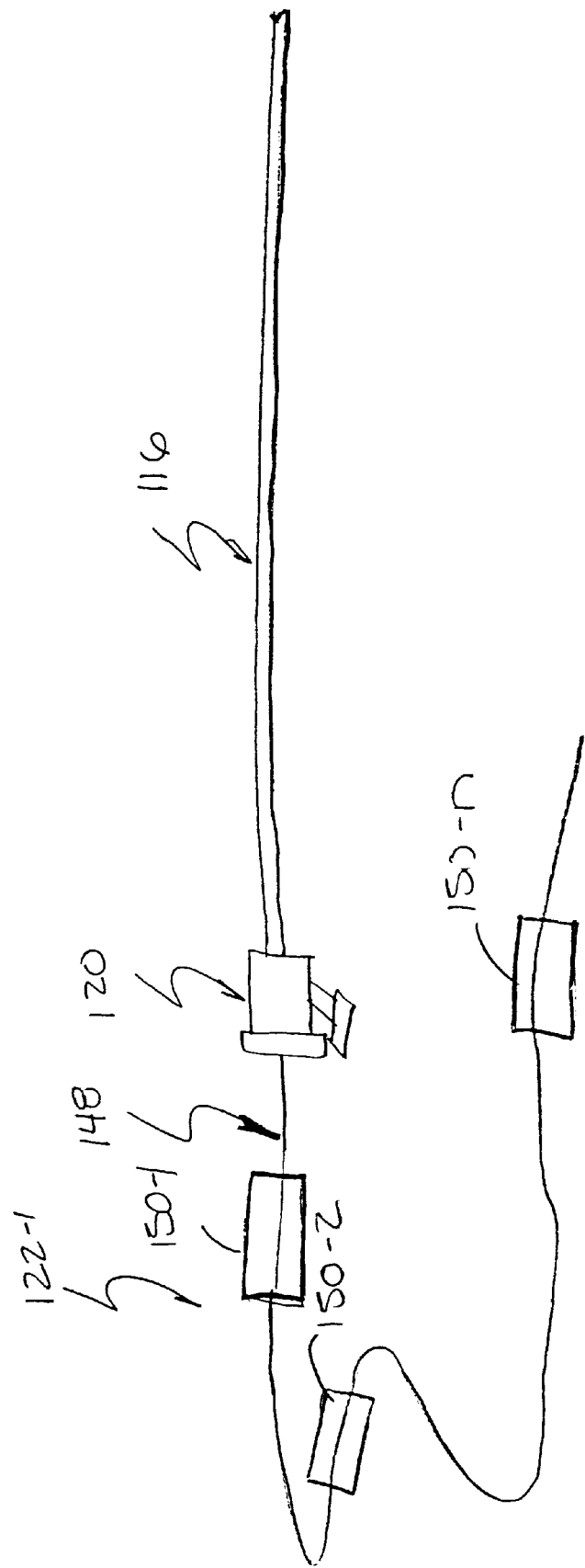

US 6,656,199 B1

MAGNETIC CLAMP ASSEMBLY FOR AN ELONGATED FLEXIBLE MEDICAL DEVICE

BACKGROUND OF THE INVENTION

The present invention relates to the field of medical devices such as elongated flexible catheter and accessory devices. In particular, the present invention relates to a magnetic clamp assembly for retaining elongated flexible medical devices in a coiled or collapsed condition and has particular application for angioplasty devices.

Catheter and other treatment devices are formed of elongated members which are relatively flexible for insertion into a body vessel of a patient for treatment. The length of various catheter or treatment devices is relatively long to track the device to a remote treatment site. For example, typically the length of an angioplasty catheter is approximately 150 cm long and a guidewire is approximately 175 cm long. Catheter and other treatment devices are sterilized for human use.

Prior to use and reuse, the catheter or other device must remain in a sterile zone or field. The extended length of catheters and other treatment devices are packaged in sterile containers in a coiled configuration. Once removed from the sterile packaging, the entire length of the device must remain in the sterile field for use and reuse. The sterile zone or field is typically a sterile cart, operating table or localized treatment area. The long length of catheters or other devices makes it awkward to control and handle the device and retain the device in the sterile field.

Angioplasty devices are intravascularly inserted into a patient for treating coronary heart disease. Angioplasty devices include an elongated catheter having a dilation balloon supported at a distal end which is inserted over an elongated guidewire. During an angioplasty procedure, often several different types of catheters are employed sequentially utilizing the same guidewire and in some cases the catheter may be alternately used several times. Once removed from the guidewire, the catheter must be kept in a sterile field for re-use. As previously discussed, the length of the catheter shaft makes it quite awkward and inconvenient to retain the catheter in the sterile field for reuse.

Various types of catheter devices used include fixed wire catheters, over-the-wire catheters and single operator exchange catheters. During an angioplasty procedure, a doctor may decide to exchange an inserted catheter device with another catheter device. To facilitate a catheter exchange with an over-the-wire catheter device, a guidewire extension can be added to the end of the guidewire or an original wire can be replaced with an exchange guidewire. It is important to assure that the length of guidewire extension or exchange guidewire remains sterile and does not drop on the floor. However, the additional length of the guidewire extension or exchange guidewire makes it difficult to retain the length of the guidewire in the sterile field.

Prior mechanical clip devices are known to retain elongated catheters in a coiled configuration for use and reuse. These devices can be cumbersome to use and can require two hands to operate. The present invention address these and other problems and has wide application for various angioplasty catheter devices such as cutting devices, fiber optic catheters, ultrasound probes and other treatment devices.

SUMMARY OF THE INVENTION

The present invention relates to a magnetic clamp assembly for an elongated flexible medical device or treatment device. The clamp assembly includes magnetic clamp members operably coupled to clamp a portion of the flexible medical device to secure the medical device during treatment.

BRIEF DESCRIPTION OF THE DRAWINGS

FIG. 1 is an illustration of an angioplasty catheter system in a vascular lumen of a patient.

FIG. 2 is a diagrammatic illustration of a catheter including an embodiment of a magnetic clamp of the present invention.

FIG. 3 is a diagrammatic illustration of the catheter of FIG. 2 secured in a coiled configuration by the magnetic clamp of the present invention.

FIG. 4 is a diagrammatic illustration of the catheter of FIG. 2 secured in a looped configuration by the magnetic clamp of the present invention.

FIG. 5 is a diagrammatic illustration of an embodiment of clamp members of a magnetic clamp of the present invention.

FIGS. 6-1 through 6-3 are cross-sectional views of various embodiments of clamp members coupled to a segment of the catheter.

FIG. 8 is a diagrammatic illustration of a guidewire including an embodiment of a magnetic clamp of the present invention.

FIG. 9 is a diagrammatic illustration of the guidewire of FIG. 8 secured in a coiled configuration by the magnetic clamp of the present invention.

FIGS. 10-1 through 10-3 are illustrations of various embodiments of clamp members on a segment of the guidewire.

FIG. 11 is a diagrammatic illustration of a guidewire including multiple spaced clamp members along a length thereof.

DETAILED DESCRIPTION OF THE ILLUSTRATIVE EMBODIMENTS

Figure 7:
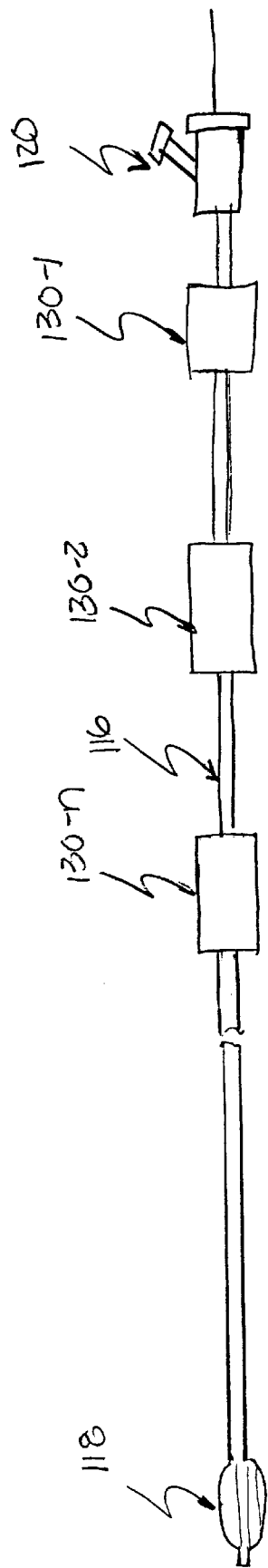
FIG. 7 is a diagrammatic illustration of a catheter including multiple spaced clamp members along a length thereof.

The present invention generally relates to elongated flexible devices inserted-into a body lumen or vessel for treatment. Such devices are formed of a biocompatible material and are typically packaged in a sterile condition. Once devices are removed from the sterile packaging, it is important that the devices remain in a sterile environment for use. If the devices become contaminated prior to use or reuse, the device may need to be discarded which can increase the cost of treatment and possibly delay treatment.

Angioplasty devices are used to treat heart disease. FIG. 1 illustrates embodiments of coronary angioplasty devices for treating a lesion 100 in a coronary vessel 102. As shown, angioplasty treatment devices include a guide catheter 106. The guide catheter 106 is formed of a flexible tubular member having an elongated length extending from a proximal manifold 108 to a distal end 110. The guide catheter is inserted into a vascular lumen 112 at a femoral artery and advanced until the distal end 110 of the guide catheter 106 is adjacent a mouth of the coronary vessel 102. The inserted guide catheter 106 provides a conduit for inserting a treatment catheter 114 or diagnostic catheter.

As shown in FIG. 1, treatment catheter 114 is an over-the-wire balloon catheter. The balloon catheter includes a flexible catheter shaft 116 having an elongated length extending between a proximal end and a distal end. A dilatation balloon 118 is supported at the distal end of the catheter shaft 116 and the catheter shaft 116 includes a proximal manifold 120. As shown, an elongated flexible guidewire 122 extends through a guidewire lumen (not shown) in shaft 116 to facilitate placement of the treatment catheter 114 as will be explained. For dilatation, an inflation device 123 is coupled to an inflation lumen (not shown) at proximal manifold 120 to inflate balloon 118.

The length of the catheter shaft 116 is sufficiently long to extend from the femoral artery to the treatment vessel 102. The length of guidewire 122 is longer than shaft 116 so that a proximal portion 124 extends beyond the proximal manifold 120 (beyond the guidewire lumen in shaft 116) for gripping the guidewire 122 for use. The guidewire 122 extends along shaft 116 and includes a distal portion 126 which extends distally beyond shaft 116 to track the balloon 118 (or other treatment device) across the lesion. Typically the length of an angioplasty catheter is approximately 150 cm long and a guidewire 122 is approximately 175 cm long.

For treatment, catheter 114 is advanced through guide catheter 106, with the guidewire 122 extending through the catheter shaft 116, to the distal end of the guide catheter 106. Guidewire 122 is independently advanced into the restricted coronary vessel 102 to cross the lesion 100. Guidewire 122 is independently advanced by manipulating the proximal portion 124 of the guidewire 122 extending outside the proximal manifold 120. Thereafter, catheter shaft 116 is advanced along guidewire 122 to position the balloon 118 (or other treatment device) across the lesion 100.

As previously, described, for use, the device must be kept sterile for insertion into a body vessel or lumen. During treatment, devices may be temporarily withdrawn or removed. Temporarily withdrawn devices or catheters must be kept sterile for reuse. During a treatment procedure, a surgeon or doctor may be using or handling multiple devices and the length of such devices can make it difficult to manage or control the devices so that the entire length of every device is maintained within the sterile field for the entire procedure.

MAGNETIC CLAMP DEVICE FOR A CATHETER SHAFT

FIGS. 2–3 illustrate a treatment catheter 114-1 incorporating a magnetic clamp 128 for coiling or collapsing an extent of the elongated length of flexible shaft 116 where like numbers are used to identify like parts in the previous FIG. As shown in FIG. 2, the clamp device 128 includes magnetically attracted clamp members 130-1, 130-2 illustrated diagrammatically in FIGS. 2–3. As shown in FIG. 2, clamp member 130-1 is formed along a first portion 132-1 of the catheter shaft 116 and clamp member 130-2 is formed along a second portion 132-2 of the catheter shaft 116 spaced from clamp member 130-1. The magnetically attracted clamp members 130-1, 130-2 are spaced to cooperatively form the magnetic clamp 128 as illustrated in FIG. 3.

As shown in FIG. 3, the magnetic clamp 128 secures a segment of the catheter shaft 116 in a coiled configuration to collapse an extended length of the catheter shaft so that the catheter is more compact and thus, easy to control and maintain in the sterile field. The magnetic attraction between the clamp members 130-1, 130-2 is designed to secure or clamp the shaft 116 in the coiled configuration yet allow the clamp members 130-1, 130-2 to easily separate to release the catheter shaft 116 from its coiled configuration. Thus, the magnetic clamp device described can be easily operated to clamp the catheter shaft 116 in a coiled configuration and easily released to straighten the catheter shaft 116 for use.

In the embodiment shown, clamp member 130-1 is positioned midshaft and clamp member 130-2 is positioned proximate to proximal manifold 120 to coil the catheter for sterile use. Clamp members 130-1, 130-2 can be positioned at alternate locations to coil various portions of the catheter shaft 116 and to connect the shaft 116 in alternate collapsed profiles, such as in a looped profile as illustrated in FIG. 4.

The magnetically attracted clamp members 130-1, 130-2 can be formed of a magnetically responsive material and a magnetically active material. A magnetically active material is a material having a magnetic field, such as a permanent magnet or electromagnet. A magnetically responsive material is a material which is attracted to a magnetically active material. In one embodiment, having a proximal clamp member 130-2, and a midshaft (or distal) clamp member 130-1, the proximal clamp member 130-2 is formed of a magnetically active material and the midshaft (or distal) clamp member 130-1 is formed of a magnetically responsive material so that the magnetically active material remains outside the patient during treatment.

An example of a magnetically active material includes a neodymium magnet and examples of a magnetically responsive material include a vanadium permedur material, Hyperco®, or other ferromagnetic material. The magnetically active material or magnetically responsive material can be a solid magnet or ferromagnet or magnetic particles can be embedded in a polymer base material to form the active magnet or responsive magnetic material. Alternatively, both clamp members 130-1, 130-2 can be formed of magnetically active material, as illustrated schematically in FIG. 5, in which a magnetic pole of clamp member 130-1 is attracted toward the opposite magnetic pole of clamp 130-2. The clamp members 130-1, 130-2 are magnetically attracted to selectively clamp portions of the flexible catheter shaft 116 as previously described.

The clamp members 130-1, 130-2 can be connected to or formed with shaft 116 or manifold 120. FIGS. 6-1 through 6-3 illustrate alternate embodiments of clamp members 130 formed on a portion of the flexible shaft 116. Flexible shaft 116 is typically formed of a polymer material. In the illustrated embodiments, clamp members 130 are formed of an annular ring or tube 140 of a magnetically active or magnetically responsive material. In the embodiment of FIG. 6-1, ring 140 extends about an outer perimeter 141 of shaft 116. In FIG. 6-2, ring 140 is seated in an outer recess 142 about perimeter 141 of catheter shaft 116 to provide a smooth profile for the catheter shaft 116. In FIG. 6-3, ring 140 is seated in an inner recess 144 surrounding a lumen 146 along shaft 116. Clamp members 130 can be formed in a proximal strain relief (not shown) or manifold 120. Alternatively, clamp members 130-1, 130-2 can be formed separately from shaft 116 and fastened or clipped to the catheter shaft 116 for use. For example, clamp members 130-1, 130-2 can be fastened to shaft 116 when the catheter is prepared for use and remain on the shaft 116 for use as necessary.

As illustrated in FIG. 7, multiple spaced clamp members 130-1, 130-2, 130-n can be spaced along the catheter shaft 116 to provide flexibility for coiling or collapsing the catheter shaft 116 in different configurations. As previously described, clamps 130-1, 130-2, 130-n can be formed of a magnetically active material. In one embodiment, a proximal clamp member 130-1 can be formed of a magnetically active material and distal clamp members 130-2 to 130-n can be formed of a magnetically responsive material. Alternatively, magnetically active or responsive clamp members can be intermittently dispersed along portions of the catheter shaft 116. Thus, as described, the magnetic clamp is easily operable to retain the elongated shaft 116 in a collapsed profile and application is not limited to the particular configurations shown.

MAGNETIC CLAMP DEVICE FOR A GUIDEWIRE

Often times, it is desirable to exchange one catheter 114 for another catheter during a treatment procedure. It is usually preferred that the catheter 114 be withdrawn over an inserted guidewire so that the guidewire remains in place across the stenosis 100 to advance the next catheter across the stenosis 100 for treatment. During the exchange, a proximal portion of the guidewire which is external to the patient must be exposed at all times while the catheter 114 is withdrawn so that the operator can grip the guidewire to control the position of the guidewire relative to the stenosis. However, in an over-the-wire catheter, the guidewire 122 extends through a guidewire lumen which is longer than the proximal portion of the guidewire external to the patient. Thus, if the physician were to fully withdraw the catheter while leaving the guidewire in place, the catheter 114 would completely cover the external portion of the guidewire 122 and the surgeon or doctor would not be able to grip the guidewire during the exchange.

Thus, a longer exchange guidewire or guidewire extension (hereinafter, exchange length guidewire 122-1) can be used to maintain control of the guidewire during the exchange process. For example, an exchange wire, having a length of about 300 cm or a guide wire extension having a length about 125–150 cm can be used. The additional length of the exchange guidewire or extension provides an external guidewire portion which is longer than the length of the guidewire lumen of the inserted catheter to allow the physician to grip the inserted guidewire 122-1 while the catheter 114 is removed over the guidewire 122-1. The long length of the exchange length guidewire 122-1, however, makes it difficult to maintain the entire length of the guidewire 112-1 in the sterile field during treatment.

FIGS. 8–10 illustrate alternate embodiments of a magnetic clamp device for collapsing a proximal length of the exchange length guidewire 122-1 so that it remains in the sterile field during treatment where like numbers are used to refer to like parts in the previous FIGS. As shown in FIG. 8, a proximal length 148 of the exchange length guidewire 122-1 extending beyond the proximal end of the catheter shaft 116 and outside the patient includes clamp members 150-1, 150-2 illustrated diagrammatically which cooperatively form clamp 152 as shown in FIG. 9. Clamp member 150-1 is formed along a first portion of the guidewire 122-1 and the second clamp member 150-2 is formed along a second portion of the guidewire 122-1 spaced from clamp member 150-1 as shown. The clamp members 150-1, 150-2 are spaced to cooperatively form magnetic clamp 152 to retain the proximal length 148 of the guidewire 122-1 in a coiled or collapsed profile as shown in FIG. 9. Clamp members 150-1, 150-2 can be active magnets or alternatively, clamp members 150-1, 150-2 can include an active magnet and a magnetically responsive segment as previously described for clamp members 130-1, 130-2.

FIGS. 10-1 through 10-3 illustrate alternate embodiments for clamp members 150-1, 150-2 formed along the proximal length of guidewire 122-1. Clamp members 150-1, 150-2 can be formed of an annular ring 153 extending about an outer perimeter. 154 of guidewire 122-1 as shown in FIG. 10-1 or an annular ring 156 seated in recess 158 extending about perimeter 154 of the guidewire 122-1 as shown in FIG. 10-2. Alternatively, as shown in FIG. 10-3, portions of the guidewire 122-1 can be formed of a magnetic segment 160 adhesively connected to guidewire segments 162-1, 162-2 to form guidewire 122-1. Annular rings 153, 156 or magnetic segment 160 can be formed of an active magnet or a magnetically responsive material such as a Hyperco®. In one embodiment, clamp member 150-1 is an active magnet and clamp member 150-2 is a magnetically responsive segment.

In an alternate embodiment, multiple clamp members 150-1, 150-2, 150-n extend along the proximal length of the exchange length guidewire 122-1 as illustrated in FIG. 11 to coil different lengths of the guidewire 122-1. Multiple clamp members 150-1, 150-2, 150-n can include an active magnet and a plurality of magnetically responsive segments spaced from the active magnet to retain guidewire 122-1 in a coiled profile as illustrated in FIG. 9 or other collapsed profiles (not shown).

MAGNETIC CLAMP DEVICE INCLUDING A MAGNETIC TABLE AND CLAMP MEMBER

Figure 12:
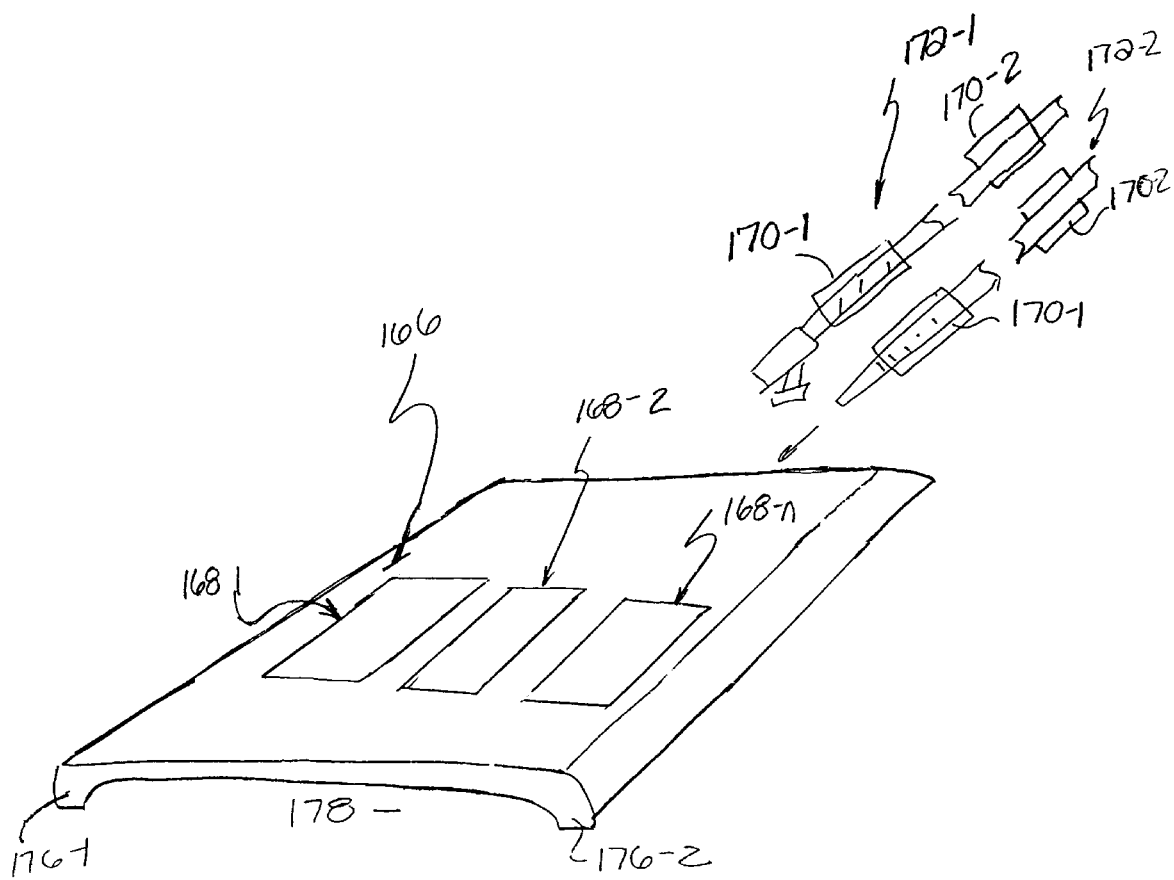
FIG. 12 is an illustration of an embodiment of a magnetic clamp device including a table supporting clamp members.

FIG. 12 illustrates another embodiment of a magnetic clamp device for securing a medical device prior to, during or subsequent to treatment. The device includes a table or tray 166 including magnetic clamp members 168-1, 168-2, 168-n (illustrated schematically) which cooperate with clamp members 170-1, 170-2 (illustrated schematically) on treatment devices 172-1, 172-2 as shown. Clamp members 138 and 170 magnetically attract or couple to secure the treatment device or catheter 172 relative to table 166. Clamp members 168, 170 can be formed of an active magnet or a magnetically responsive material. In one embodiment, clamp members 170 are formed of a magnetically responsive material and clamp members 168 are active magnets, although application is not limited to any specific embodiment shown.

The table 166 may be sterile or covered with a sterile drape (not shown) so that treatment devices are maintained or stored in a sterile environment or field for use during treatment. Treatment devices 172 can include syringes, guidewires, catheters, guide catheters, grips, Y-adapters, stents, rotablator and other treatment devices and any number of clamp members 168 can be supported on table 166 to secure multiple treatment devices or a single treatment device.

In the embodiment illustrated in FIG. 12, table 166 includes base rails 176-1, 176-2 along a length thereof separated by channel 178 which are contoured to rest on a patient's chest or abdomen or over a leg of a patient. In the embodiment shown, rails 176-1, 176-2 extend along an entire length of table 166 although application is not limited to the specific embodiment shown.

Figure 13:
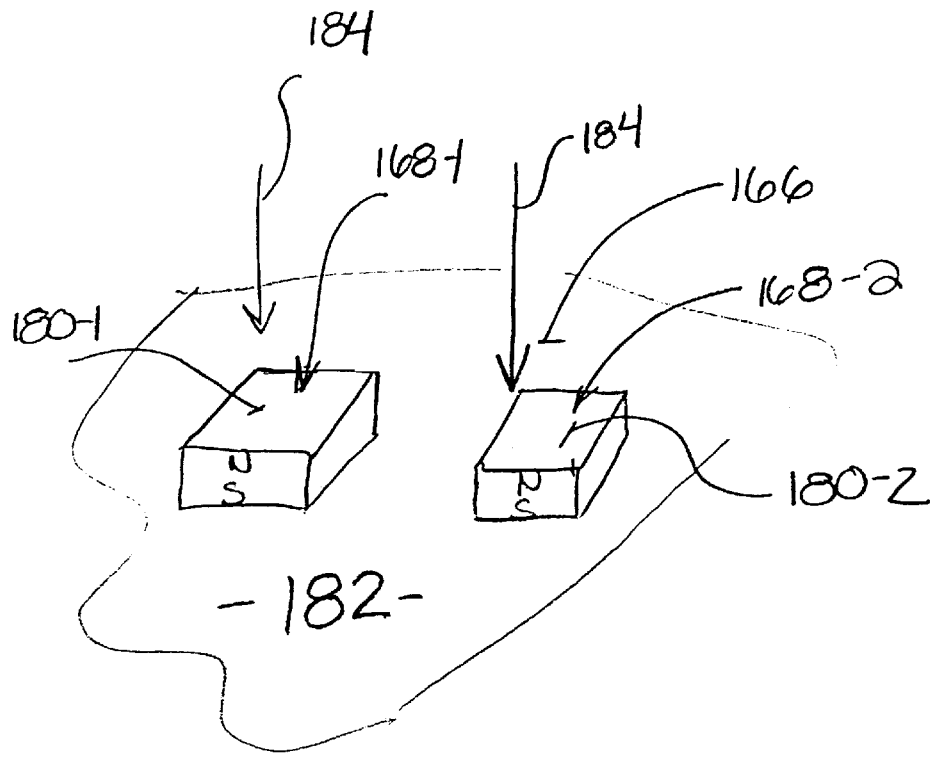
FIG. 13 is an illustration of an embodiment of clamp members on the table illustrated in FIG. 12.
Figure 14:
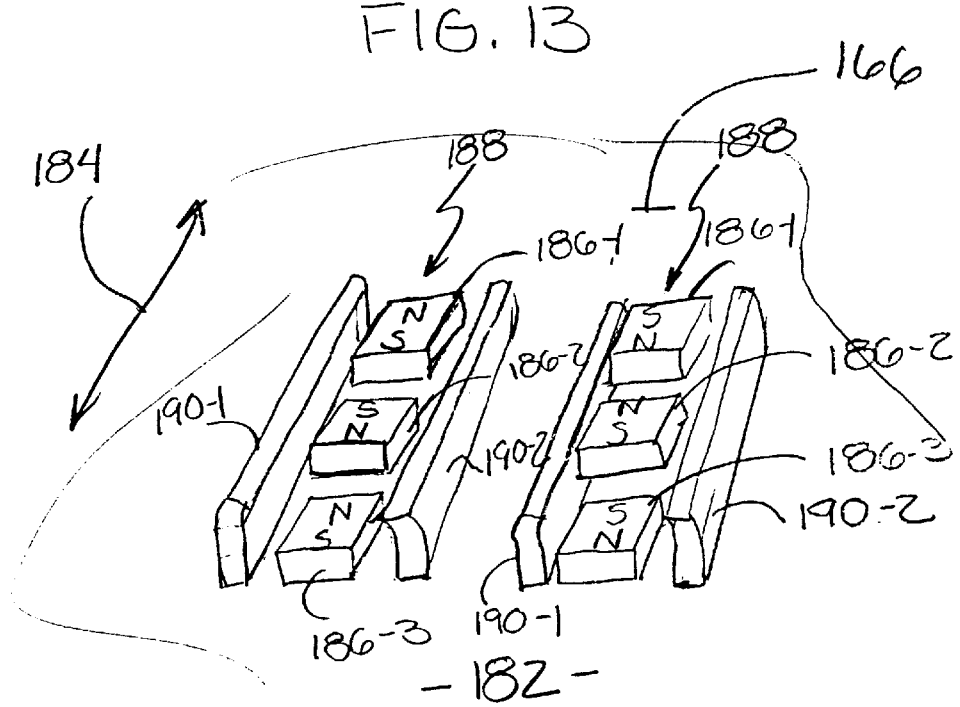
FIG. 14 is an illustration of an embodiment of clamp members on the table illustrated in FIG. 12.

FIGS. 13–14 illustrate alternate clamping embodiments for clamp members 168. As shown in FIG. 13, clamp members 168 include active magnets 180-1, 180-2 arranged to magnetically attract responsive segments on a treatment device 172. As shown, poles N,S of active magnets 180-1, 180-2 are orientated so that the flux path is perpendicular to surface 182 of table 166. The perpendicular orientation of the flux path and poles N, S provides a relatively strong attractive force between the active magnets 180 and magnetically responsive segments on the treatment device in a downward direction toward surface 182 of table 166 as illustrated by arrows 184.

In one embodiment, the treatment device includes multiple spaced clamp members 170-1, 170-2 (as shown in FIG. 12) formed of magnetically responsive segments. The spaced clamp members 170-1, 170-2 can be magnetically attracted to a single active magnet 180-1 on table 116 to secure spaced portions of the treatment device relative to table 166 or alternatively, spaced clamp members 170-1, 170-2 can be secured to multiple active magnets 180-1, 180-2 to clamp an elongated portion of a treatment device to table 166 in a coiled or collapsed profile. Alternatively, a single clamp member 170 on treatment device can be secured to a single active magnet clamp member 180-1 or 180-2 on table 166.

Figure 15:
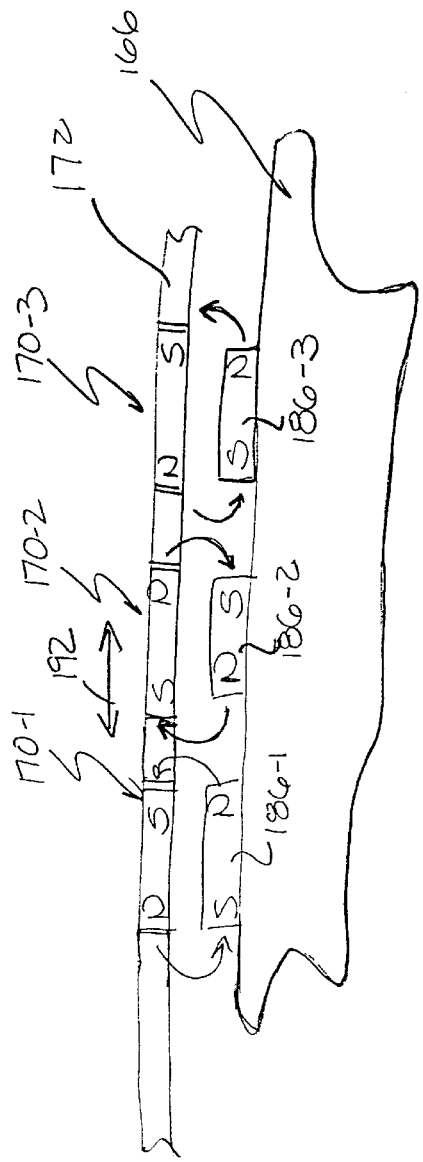
FIG. 15 is a detailed illustration of the clamp members of FIG. 14 including magnets having alternating polarity.

FIGS. 14–15 illustrates an alternate clamping embodiment for clamp members 168 supported on table 166. In the embodiment shown in FIGS. 14–15, each clamp member 168-1, 168-2 can include a plurality of spaced active magnet segments 186-1, 186-2, 186-3 having alternating polarity. In the embodiment shown in FIG. 14, the active magnet segments 186-1, 186-2, 186-3 are arranged in a slot or channel 188 formed between extending walls 190-1, 190-2. Magnet segments 186-1, 186-2, 186-3 are arranged so that poles N,S are orientated so that the flux path and poles are essentially parallel to table surface 182. As shown, magnet segments 186-1, 186-2, 186-3 are arranged with alternating polarity. For example, in the embodiment shown, magnet segments 186-1, 186-3 nave a first polarity or pole orientation and magnet segment 186-2 has a second opposite polarity or pole orientation to secure a treatment device 172 relative to table 166 as will be described.

For operation of the embodiment illustrated in FIGS. 14–15, clamp members 170-1, 170-2, 170-3 on treatment devices 172 are formed of magnetically responsive segments spaced similar to active magnets 186-1, 186-2, 186-3. Responsive segments.170-1, 170-2, 170-3 on the treatment device are formed of a magnetically permeable material capable of being magnetized. The interaction of the active magnets 186-1, 186-2, 186-3 with the magnetically responsive segments 170-1, 170-2, 170-3 on the treatment device provides a flux path through segments 170-1, 170-2, 170-3 to attract segments 170-1, 170-2, 170-3 toward active magnets 186-1, 186-2, 186-3.

The alternating polarity of the active magnets 186-1, 186-2, 186-3 provide a longitudinal restrictive force in a direction illustrated by arrow 192 as shown in FIG. 15. For example, movement of segments 170-1, 170-2, 170-3 is restricted due to the opposite polarity of magnets 186-1, 186-2, 186-3. Thus, in one embodiment for an elongated treatment device, a portion of an elongated treatment device is coiled or collapsed and the collapsed portion is inserted into slot 188 with the magnetically responsive segments on the treatment device aligned with the active magnet segments 186-1, 186-2, 186-3 to retain the device in a collapsed profile during treatment.

In the embodiment shown, magnet segments 186-1, 186-2, 186-3 are aligned along a longitudinally extending axis in a longitudinally aligned slot 188 formed between longitudinally aligned walls 190-1, 190-2. Although a particular, longitudinal alignment is shown, application is not limited to the longitudinal alignment shown. For example, magnet segments 186-1, 186-2, 186-3 can be spaced along a curved axis (not shown). Although FIGS. 13–14, illustrate specific embodiment and pattern of clamp members 168, application is not limited to the specific embodiments or patterns shown.

CLAMP DEVICE FOR USE WITH A MAGNETIC CAPTIVATION TOOL

Magnetic captivation tools 200 have been developed to facilitate a catheter exchange for an over-the-wire catheter without use of an exchange length guidewire 122-1 so that a standard length guidewire can be used. Such tools 200 include a plurality of active magnets 202 (illustrated diagrammatically in FIG. 16) coupled along an elongated channel. Magnetically responsive segments are formed along a proximal length of guidewire and are spaced similar to the spacing between magnets 202. In the particular embodiment, active magnets 202 are spaced with alternating polarity as previously described with reference to FIG. 15 to secure guidewire relative to the captivation tool by the interaction between the plurality of magnets 202 and the magnetically responsive segments on the guidewire. To facilitate an exchange, a proximal portion of guidewire 122-2 is inserted through the channel of the captivation tool 200 so that the magnetically responsive segments are aligned with the magnets 202 on the tool 200 to hold the guidewire in place and restrict longitudinal movement of the guidewire 122-2 as previously described in reference to FIG. 15. For a catheter exchange, catheter 114 is withdrawn over the secured guide wire 122-2 through the channel of the captivation tool 200 having magnets 202 holding the guidewire 122 in place.

Figure 16:
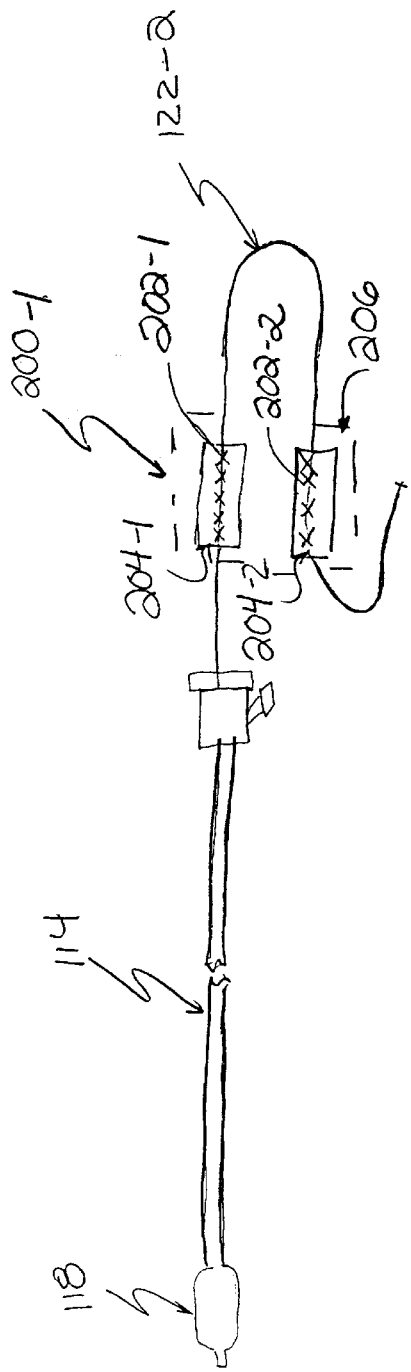
FIG. 16 is an illustration of an embodiment of a magnetic clamp device incorporated with a magnetic captivation tool for facilitating a catheter exchange.

The captivation tool 200-1 of the present invention incorporates a clamp for collapsing a length of guidewire 122-2 as illustrated in FIG. 16. As shown schematically in FIG. 16, tool 200-1 includes multiple spaced magnetic captivation segments 204-1, 204-2 each including a plurality of magnets 202-1, 202-2 of alternating polarity which form multiple clamp segments and the guidewire 122-2 includes multiple spaced magnetically responsive segments (not shown) or clamp members spaced to align with multiple captivation segments 204-1, 204-2 in a collapsed or coiled profile.

In particular, the captivation segments 204-1, 204-2 are oriented to engage spaced magnetically responsive segments on the guidewire 122-2 to connect guidewire 122-2 in a coiled or looped profile as shown. For example, in one embodiment, captivation segments 204-1, 204-2 can be formed on opposed sides or faces of an integral tool block 206 forming the captivation tool as illustrated diagrammatically in FIG. 16 or spaced on a single face of a tool block 206. Captivation segments can be formed on faces of multiple tool blocks (not shown) which are connected to form the captivation tool having multiple spaced captivation segments 204-1, 204-2. Alternatively, multiple spaced captivation segments 204-1, 204-2 can be formed on a planar surface of a table, such as the table illustrated in FIGS. 12–14. Although a particular coiled arrangement is shown, application is not limited to the particular arrangement shown.

Although the present invention has been described with reference to preferred embodiments, workers skilled in the art will recognize that changes may be made in form and detail without departing from the spirit and scope of the invention.

What is claimed is:

1. A catheter comprising:
   a flexible shaft having an elongated length extending between a proximal end and a distal end;
   a first clamp member on a first portion of the elongated length of the flexible shaft; and
   a second clamp member on a second portion of the elongated length of the flexible shaft spaced from the first clamp member and the first and second clamp members being magnetically attracted to form a magnetic clamp to connect the first and second portions of the flexible shaft.

2. The catheter of claim 1 wherein one of the first or second clamp members is an active magnet and another of the first or second clamp members is formed of a magnetically responsive material.

3. The catheter of claim 1 and including at least one additional clamp member on the flexible shaft spaced from the first and second clamp members and the at least one additional clamp member being magnetically attracted to at least one of the first or second clamp members.

4. A combination comprising:
   a flexible guidewire having an elongated length extending between a proximal end and a distal end;
   a first clamp member on a first portion of the elongated length of the flexible guidewire; and
   a second clamp member on a second portion of the elongated length of the flexible guidewire spaced from the first clamp member and the first and second clamp members being magnetically attracted to form a magnet clamp to connect the first and second portions of the flexible guidewire.

5. The combination of claim 4 wherein the first and second clamp members are formed along a proximal portion of the guidewire.

6. The combination of claim 4 wherein the guidewire is a guidewire extension connectable to a standard guidewire for a catheter exchange.

7. A medical device comprising:
   a relatively rigid surface portion having a proximal end, a distal end and opposed sides and the surface portion having at least one magnetic clamp member formed of a magnetic material; and
   first and second base rails coupled to the relatively rigid surface portion having a proximal end and a distal end and a length therebetween and the first and second base rails spaced to form a channel between the opposed sides of the relatively rigid surface portion.

8. The medical device of claim 7 wherein the surface portion includes a plurality of magnetic clamp members.

9. The medical device of claim 7 wherein the at least one magnetic clamp member is formed of an active magnet having a magnetic field.

10. The medical device of claim 9 wherein the active magnet is oriented so that a flux path of the magnet is perpendicular to the surface portion to provide an attractive force toward the surface portion.

11. The medical device of claim 7 wherein the surface portion includes a plurality of spaced active magnets of alternating polarity.

12. The medical device of claim 11 wherein the plurality of spaced active magnets are orientated so that a flux path of the plurality of spaced magnets is parallel to the surface portion.

13. The medical device of claim 11 wherein the plurality of spaced magnets are spaced along a longitudinal axis.

14. In combination:
   at least one surgical instrument including at least one clamp member along a portion thereof; and
   a relatively rigid tray having a surface portion including at least one clamp member, and the clamp member on the at least one surgical instrument being magnetically attracted to the clamp member on the surface portion of the tray.

15. The combination of claim 14 wherein the tray includes a plurality of magnetic clamp members.

16. The combination of claim 14 wherein the at least one clamp member on the surface portion of the tray is formed of an active magnet and the at least one clamp member on the at least one surgical instrument is formed of a magnetically responsive material.

17. The combination of claim 14 wherein the at least one surgical instrument includes a plurality of spaced clamp members along an elongated flexible length of a shaft portion of the at least one surgical instrument formed of a magnetically responsive material.

18. The combination of claim 14 wherein the surface portion of the tray includes a plurality of spaced magnet segments of alternating polarity and the at least one surgical instrument includes a plurality of spaced magnetically responsive segments spaced to align with the plurality of spaced magnet segments on the surface portion of the tray.

19. The combination of claim 18 wherein the plurality of spaced magnet segments on the surface portion of the tray extend along a longitudinally aligned axis.

20. In combination:
   an elongated flexible medical device including a flexible shaft portion having a proximal end and a distal end and a plurality of spaced magnetic clamping portions along a length thereof between the proximal and distal ends;
   a clamp device including a device body having a plurality of magnet clamping segments on spaced surface portions oriented to magnetically engage the magnetic clamping portions on the elongated flexible medical device to secure the flexible medical device in a collapsed profile.

21. The combination of claim 20 wherein the magnetic clamping portions on the elongated flexible medical device are formed of a magnetically responsive material.

22. The combination of claim 20 wherein the device body includes at least one of a block, multiple connected blocks, or a table and the spaced surface portions are formed on multiple faces of the block, or are spaced on a single face of the block, or formed on a face of each of the multiple connected blocks, or on a surface of the table.

23. The combination of claim 20 wherein the plurality of magnetic clamping segments include a plurality of magnets arranged in alternating polarity.

24. A method for treating a patient comprising steps of:
   providing an elongated flexible catheter device;
   collapsing the elongated catheter device; and
   magnetically clamping the elongated catheter device in a collapsed profile.

25. The method of claim 23 wherein collapsing the elongated catheter device includes coiling a length of the elongated flexible catheter device.

26. A method for treating a patient comprising steps of:
   providing an elongated flexible catheter device;
   inserting the elongated flexible catheter device into a patient for treatment;

withdrawing the elongated flexible catheter device;
collapsing the withdrawn catheter device; and
magnetically clamping the catheter device in a collapsed profile.

27. A method for treating a patient comprising steps of:
inserting an elongated flexible catheter device having an elongated catheter shaft into a patient for treatment;
providing an exchange length guidewire extending through the elongated catheter shaft;
collapsing a portion of the exchange length guidewire and magnetically clamping the collapsed portion;
withdrawing the elongated flexible catheter device over a portion of the exchange length guidewire;
releasing the clamped portion of the exchange length guidewire; and
removing the catheter device from the exchange length guidewire.

28. A method for treating a patient comprising steps of:
inserting an elongated flexible catheter device having an elongated catheter shaft into a patient for treatment;
providing an exchange length guidewire extending through the elongated catheter shaft;
withdrawing the elongated flexible catheter device over the exchange length guidewire; and
collapsing a portion of the exchange length guidewire and magnetically clamping the collapsed portion.

29. A method for treating a patient comprising steps of:
inserting a flexible elongated catheter device having a clamp member on a proximal end thereof into a patient while retaining the clamp member external to the patient; and
magnetically clamping the clamp member on the elongated flexible catheter device to a cooperating clamp member on a table.

30. A medical device comprising:
a device body having a relatively flexible elongated shaft portion having a proximal end, a distal end and an elongated length therebetween;
a first clamp member; and
a second clamp member along the shaft portion spaced from the first clamp member and the first and second clamp members being magnetically attracted to form a magnetic clamp to clamp the shaft portion.

31. The medical device of claim 30 wherein the first clamp member is along a proximal end of the device body and the second clamp member is distally spaced therefrom.

32. The medical device of claim 20 and including at least one additional clamp member on the device body spaced from the first and second clamp members and the at least one additional clamp member being magnetically attracted to at least one of the first or second clamp members.

33. The medical device of claim 30 wherein one of the first or second clamp members is an active magnet and another of the first or second clamp members is formed of a magnetically responsive material.

34. The medical device of claim 30 wherein at least one of the first or second clamp members is formed of a magnetic tube.

* * * * *

UNITED STATES PATENT AND TRADEMARK OFFICE
CERTIFICATE OF CORRECTION

| | |
|---|---|
| PATENT NO. | : 6,656,199 B1 |
| DATED | : December 2, 2003 |
| INVENTOR(S) | : Lafontaine |

It is certified that error appears in the above-identified patent and that said Letters Patent is hereby corrected as shown below:

Column 10,
Line 61, delete "23" and insert -- 24 --.

Signed and Sealed this

Twenty-fourth Day of May, 2005

JON W. DUDAS
*Director of the United States Patent and Trademark Office*